United States Patent [19]
Nakanishi et al.

[11] 3,965,111
[45] June 22, 1976

[54] TRIAZOLOTHIENODIAZEPINE COMPOUNDS

[75] Inventors: Michio Nakanishi, Oita; Kazuhiko Araki, Fukuoka; Tetsuya Tahara, Fukuoka; Masami Shiroki, Fukuoka, all of Japan

[73] Assignee: Yoshitomi Pharmaceutical Industries, Ltd., Osaka, Japan

[22] Filed: Oct. 30, 1972

[21] Appl. No.: 301,910

[30] Foreign Application Priority Data
Oct. 30, 1971 Japan.............................. 46-86663

[52] U.S. Cl...................... 260/308 C; 260/239.3 B; 260/247.1 L; 260/268 TR; 260/293.57; 260/332.2 A; 260/332.3 P; 424/248; 424/250; 424/267; 424/269
[51] Int. Cl.²....................................... C07D 495/04
[58] Field of Search................................ 260/308 C

[56] References Cited
UNITED STATES PATENTS

| | | | |
|---|---|---|---|
| 3,646,055 | 2/1972 | Hester............................. | 260/308 C |
| 3,669,959 | 6/1972 | Hromatka et al............. | 260/239.3 B |

FOREIGN PATENTS OR APPLICATIONS

| | | | |
|---|---|---|---|
| 2,107,356 | 8/1971 | Germany...................... | 260/239.3 B |

OTHER PUBLICATIONS
Hester et al., J. Med. Chem., vol. 14, pp. 1078-1081, (1971).

*Primary Examiner*—Alton D. Rollins
*Attorney, Agent, or Firm*—Sughrue, Rothwell, Mion, Zinn & Macpeak

[57] ABSTRACT

Triazolothienodiazepine compounds of the formula;

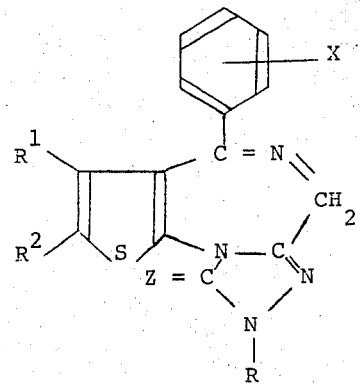

wherein X is a member selected from the group consisting of a hydrogen atom, a methyl group, a methoxy group and a trifluoromethyl group; each of $R^1$ and $R^2$ is a member selected from the group consisting of a hydrogen atom and an alkyl group having 1 to 4 carbon atoms, or $R^1$ and $R^2$ together can form a tetramethylene group, i.e.—$(CH_2)_4$—; R is a member selected from the group consisting of a hydrogen atom, an alkyl group having 1 to 4 carbon atoms, —$CONHR^3$ ($R^3$ being an alkyl group having 1 to 4 carbon atoms) and -alk-$N(R^4)(R^5)$ (each of $R^4$ and $R^5$ being a member selected from the group consisting of a hydrogen atom and an alkyl group having 1 to 4 carbon atoms, or $R^4$ and $R^5$ and N can form a heterocyclic ring; and alk being an alkylene group having 2 to 4 carbon atoms); and Z is a member selected from the group consisting of an oxygen atom and a sulphur atom; and the pharmaceutically acceptable acid addition salts thereof are disclosed. These compounds are useful as minor tranquillizers (anti-anxiety drugs), sleep inducers, and anti-epileptics.

6 Claims, No Drawings

TRIAZOLOTHIENODIAZEPINE COMPOUNDS

SUMMARY OF THE INVENTION

This invention relates to a novel and therapeutically valuable triazolothienodiazepine compound of the general formula;

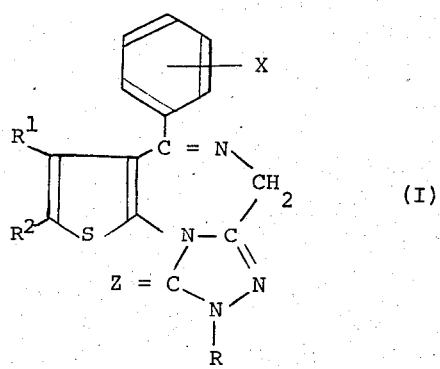

(I)

and pharmaceutically acceptable acid addition salts thereof, wherein X is a member selected from the group consisting of hydrogen atom, a halogen atom (e.g. F, Cl or Br), a methyl group, a methoxy group and a trifluoromethyl group; each of $R^1$ and $R^2$ is a member selected from the group consisting of a hydrogen atom and an alkyl group having 1 to 4 carbon atoms (e.g. methyl, ethyl, propyl, butyl or isobutyl) or $R^1$ and $R^2$ together can form a tetramethylene group, i.e. $-(CH_2-)_4-$; R is a member selected from the group consisting of a hydrogen atom, an alkyl group having 1 to 4 carbon atoms, $-CONHR^3$ ($R^3$ being an alkyl group having 1 to 4 carbon atoms) and -alk-$N(R^4)(R^5)$ (each of $R^4$ and $R^5$ being a member selected from the group consisting of a hydrogen atom and an alkyl group having 1 to 4 carbon atoms, or $R^4$ and $R^5$ and N can form a heterocyclic ring, i.e., such as a pyrrolidine, piperidine, morpholine, or N'-methylpiperazine ring, and alk being an alkylene group having 2 to 4 carbon atoms, such as ethylene, propylene, trimethylene or 2-methyltrimethylene); and Z is a member selected from the group consisting of an oxygen atom and a sulphur atom.

The compounds of general formula (I) can be produced by one of the following described methods (i) to (v)

DETAILED DESCRIPTION OF THE INVENTION i. In the case of the compounds of the general formula (I), wherein R is H or $C_{1-4}$ alkyl, a compound of the formula:

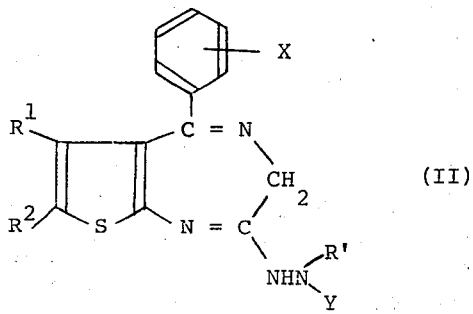

(II)

is subjected to intramolecular condensation, wherein Y is a member selected from the group consisting of an alkoxycarbonyl group (e.g. methoxy-, ethoxy- or propoxy carbonyl), an alkylcarbamoyl group (e.g. methyl-, ethyl- or propyl-carbamoyl), a dialkylcarbamoyl group (e.g. dimethyl-, diethyl- or dipropylcarbamoyl), an alkyl-thiocarbamoyl group (e.g. methyl-, ethyl- or propyl-thiocarbamoyl) and a dialkl-thiocarbamoyl group (e.g. dimethyl-, diethyl- or dipropyl-thiocarbamoyl); R' is a member selected from the group consisting of a hydrogen atom and an alkyl group having 1 to 4 carbon atoms, and the other symbols are as defined above.

The reaction is generally carried out with or without an inert solvent, such as benzene, toluene, xylene, chloroform, dichloromethane, ethyl ether, isopropyl ether, dioxane, tetrahydrofuran, dimethylformamide or pyridine, and advantageously in the presence of a catalyst such as an alkali metal compound (e.g. sodium methoxide), under heating at a temperature from 150° C to 300° C when a solvent is not used and at a boiling point of the solvent when a solvent is used, for about 0.5 to 24 hours.

ii. In the case of the compounds of the general formula (I) wherein R is H or $C_{1-4}$ alkyl, a compound of the formula:

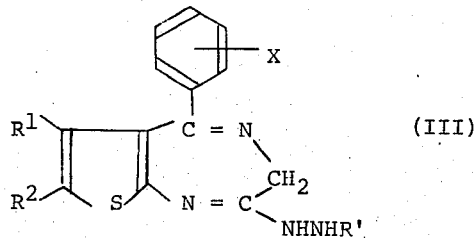

(III)

is reacted with a compound of the formula

$Z = CCl_2$   (IV)

wherein each symbol is as defined above.

The reaction is generally carried out in an inert solvent such as mentioned above, and advantageously in the presence of an acid acceptor (e.g. triethylamine or pyridine), at a temperature of from room temperature to a reflux temperature, for a period of time from 1 to 24 hours.

iii. In the case of compounds of general formula (I) wherein R is $C_{1-4}$ alkyl, a compound producible by methods (i) or (ii) above and having the formula:

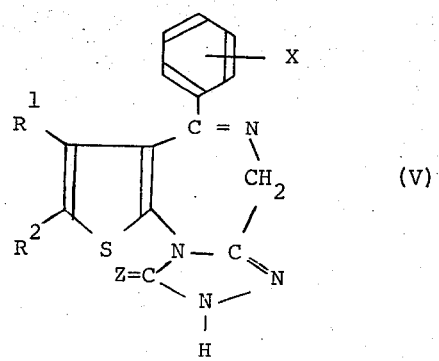

(V)

is reacted with a compound of the formula:

R″ — Q     (VI)

wherein Q is a reactive atom or group (e.g. a halogen atom, methylsulfonyloxy group or a p-tolylsulfonyloxy group; R″ is an alkyl group having 1 to 4 carbon atoms, and the other symbols are as defined above.

The reaction is usually carried out by first treating the compound of the formula (V) with an alkali metalating agent (e.g. sodium, sodium hydride or sodium methoxide) in the presence of an inert solvent such as described above, and then by reacting the resulting alkali metal salt of compound (V) with compound (VI) at a temperature of from room temperature to a reflux temperature for a period of time from 1 to 24 hours.

iv. In the case of the compounds of the general formula (I) wherein R is —CONHR³ a compound of formula (V) is reacted with a compound of the formula:

R³ —NCO     (VII)

wherein R³ is as defined above.

The reaction is usually carried out in the presence of an inert solvent, such as described above and at a temperature from 0° C to a reflux temperature for a period of from 1 to 24 hours.

v. In the case of the compounds of general formula (I) wherein R is -alk-N(R⁴) (R⁵), a compound of formula (V) is reacted with a compound of the formula:

(R⁴) (R⁵)N-alk-Q     (VIII)

wherein each symbol is as defined above.

Recommended reaction conditions are those for the method (iii).

The compounds of formula (I) can be converted into their corresponding acid addition salts in a conventional manner by treating the compounds with various inorganic and organic acids, for example, hydrochloric, sulfuric, nitric, hydrobromic, methanesulfonic, p-toluenesulfonic, acetic, oxalic, maleic, fumaric, citric, tartaric and camphor-B-sulfonic acids.

The starting compounds (II) and (III) can be prepared, for example, by conventional methods as represented by the following schematic flow sheet:

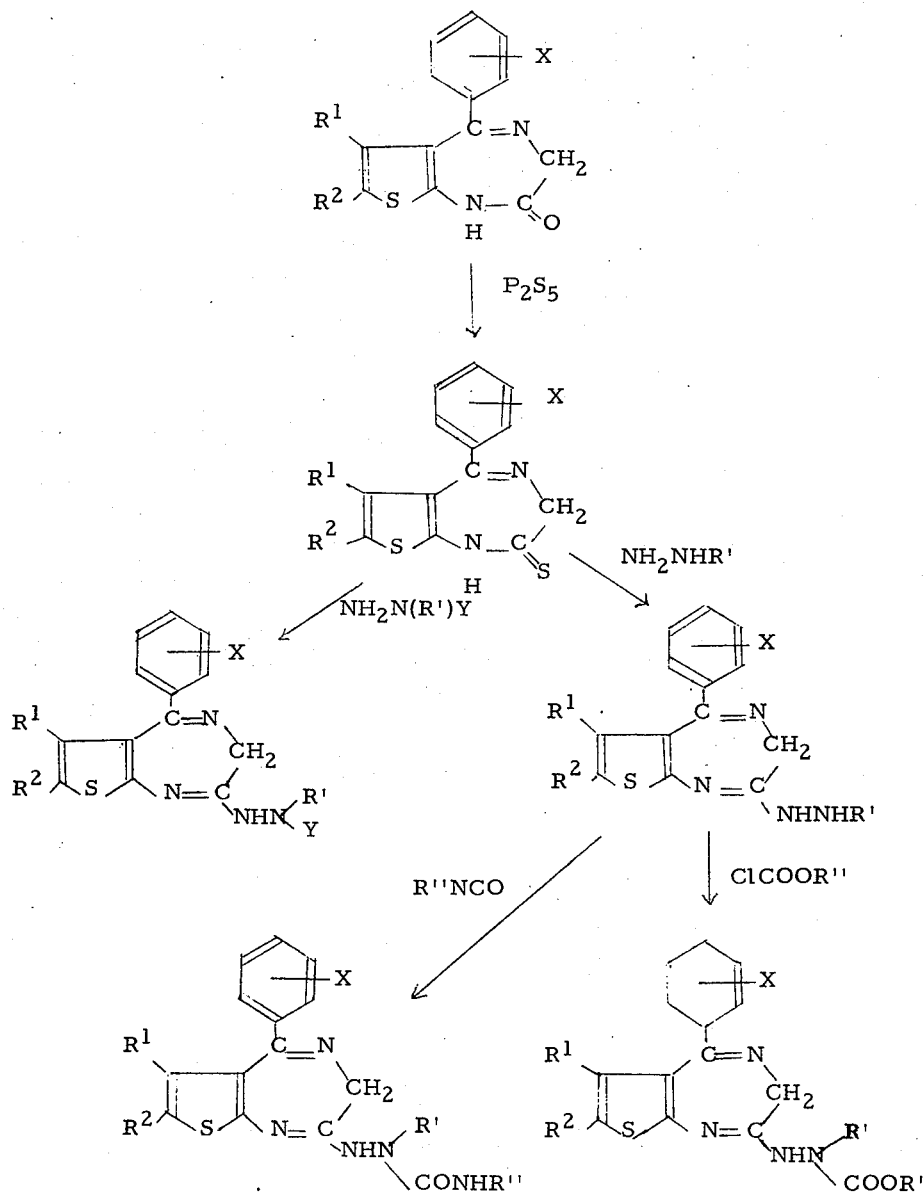

The compounds of formula (I) and the pharmaceutically acceptable acid addition salts thereof are excellent in (1) suppression of fighting behavior, (2) exhibiting an anti-pentylenetetrazole effect and (3) in exhibiting an anti-megimide effect, as shown, for example, by the following tests I. Suppression of Fighting Behavior Fighting episodes were produced in mice by the method described by Tedeschi et al in Journal of Pharmacology and Experimental Therapeutics, Vol. 125, pp. 28 ff. (1959). Groups of 8 female mice (4 pairs) were given orally, the test compound 60 minutes prior to receiving electric foot-shock for 3 minutes with 530 volts of interrupted direct current, 1.3 milliamperes, 10 Hz. Exhibiting 3 fighting episodes or less within 3 minutes were deemed to be an effective suppression by the test compound. The control mice of 81 pairs had shown the fighting episodes of 8.7 times on the average under the same conditions. The $ED_{50}$, a dose required to suppress 50% of fighting pairs was determined graphically.

II. Anti-pentylenetetrazole Effect

Pentylenetetrazole (150 mg/kg) was administered subcutaneously to groups, each of 6 mice, 15 minutes after intraperitoneal administration of the test compound. The number of dead mice were counted 3 hours after the administration of pentylenetetrazole, and then the $ED_{50}$, a dose required to reduce the number of dead mice to 50%, was determined graphically.

III. Anti-megimide Effect

Megimide (80 mg/kg) was administered subcutaneously to groups, each of 6 mice, 60 minutes after intraperitoneal administration of the test compound. The $ED_{50}$, a dose required to prevent for 3 hours, the tonic extensor convulsion induced by the administration of megimide in 50% of the animals, was determined graphically.

human adults usually ranges from about 2 to 24 mg, e.g. 1 to 12 tablets, each tablet containing 2 mg of the compound (I), in a single or multiple dose. However, the dose may vary depending upon the age, body weight, and/or severity of the condition to be treated as well as the patient's response to the medication. Therefore, the minimum amount of the compound of formula (I) required, is that, which will produce a psycotherapeutic effect.

The present invention will be better understood from the following examples, which are merely illustrative and not limitative of the present invention.

EXAMPLE 1

6-o-Chlorophenyl-8-ethyl-1,2-dihydro-4H-s-triazolo [3,4-c]thieno[2,3-e][1,4]diazepin-1-one a. 1 g of 2-ethoxycarbonylhydrazino-5-o-chlorophenyl-7-ethyl-3H-thieno[2,3-e][1,4]diazepine is dissolved in 20 ml pyridine, and 0.1g of sodium methoxide is added, and the resulting mixture is refluxed for 2.5 hours. Then, the pyridine is removed under reduced pressure, and the residue is extracted with chloroform. The extract is washed well with water, dried over anhydrous magnesium sulfate, and the solvent is removed under reduced pressure. The residue is recrystallized from a mixture of toluene and ligroin to give the title compound appearing as white crystals, melting at 199°–200° C.

The starting compound, 2-ethoxycarbonylhydrazino-5-o-chlorophenyl-7-ethyl-3H-thieno [2,3-e][1,4]diazepine, can be produced by the following procedure Diphosphorus pentasulphide (32 g) is added to a solution of 40 g of 5-o-chlorophenyl-7-ethyl-1,2-dihydro-3H-thieno[2,3-e][1,4]diazepin-2-one on 20 ml of pyridine, and the resulting mixture is stirred at 60° C for 1 hour, and then allowed to cool. Then, the reaction mixture is poured into 2 liters of ice water under cool-

| Action | Results: Compound | A | B | C |
|---|---|---|---|---|
| Suppression of Fighting Behavior | $ED_{50}$ mg/kg | 4.8 | 0.8 | 2.7 |
| Antipentylenetetrazole Effect | $ED_{50}$ mg/kg | 0.9 | 1.4 | 2.6 |
| Antimegimide Effect | $ED_{50}$ mg/kg | 1.3 | 5.7 | 7.2 |

Compounds A to C are identified below:
A: 2,8-Dimethyl-6-o-chlorophenyl-1,2-dihydro-4H-s-triazolo-[3,4-c]thieno-[2,3-e][1,4]diapezin-1-one
B: 2-Methyl-6-o-chlorophenyl-8-ethyl-1,2-dihydro-4H-s-triazolo-[3,4-c]-theno[2,3-e][1,4]diazepin-1-one hydrochloride ½ acetone
C: 6-o-Bromophenyl-8-ethyl-1,2-dihydro-4H-s-triazolo[3,4-c]-thieno[2,3-e]-[1,4]diazepin-1-one In view of the various tests conducted, including those described above, the compounds of this invention represented by the formula (I) and pharmaceutically acceptable acid addition salts thereof can be safely administered as minor tranquillizers (anti-anxiety drugs), sleep inducers and anti-epileptics in the form of a pharmaceutical preparation with a suitable and conventional pharmaceutically acceptable inert carrier or adjuvant, without adversely affecting the patient treated.

The pharmaceutical preparations can take any conventional form such as tablets, capsules or powders.

The daily dose of compound (I) or a salt thereof for ing, and the precipitate is collected by suction filtration, washed well with water and dissolved in chloroform. The chloroform solution is washed with an aqueous sodium hydrogen carbonate solution and then with water, dried over sodium sulfate, and then concentrated under reduced pressure. The residue is recrystallized from a mixture of ethanol and chloroform to give 31.4 g of 5-o-chlorophenyl-7-ethyl-1,2-dihydro-3H-thieno[2,3-e][1,4]diazepine-2-thione as yellow crystals, melting at 198°–199° C with decomposition.

A solution of 1.3 g of 5-o-chlorophenyl-7-ethyl-1,2-dihydro-3H-thieno[2,3-e][1,4]diazepine-2-thione and 0.5 g of ethoxycarbonylhydrazine in 30 ml of ethanol is refluxed for 5 hours. Then the ethanol is removed under reduced pressure, and the residue is crystallized from ligroin to give 2-ethoxycarbonylhydrazino-5-o-chlorophenyl-7-ethyl-3H-thieno[2,3-e][1,4]diazepine appearing as orange crystals. The product is recrystalized from ethanol to give the pure substance melting at 207° C, in 73% yield.

b. 100 ml of a toluene solution containing 20% phosgene is added dropwise with stirring to a suspension of 11.2 g of 2-hydrazino-5-o-chlorophenyl-7-ethyl-3H-thieno[2,3-e][1,4]diazepine and 3.6 of g of triethylamine in 50 ml toluene. The resulting mixture is stirred at room temperature for 2 hours, and then the excess phosgene is removed by refluxing the mixture with stirring under introduction of nitrogen. After cooling, water is added to the reaction mixture, and the toluene phase is washed several times with water and dried over anhydrous magnesium sulfate. The toluene is removed under reduced pressure, and the remaining jelly-like substance is crystallized from a mixture of toluene and ligroin to give the title compound appearing as white crystals. The product, when crystallized from toluene, shows a melting point of 199°–200° C.

The starting compound, 2-hydrazino-5-o-chlorophenyl-7-ethyl-3H-thieno[2,3-e][1,4]diazepine can be produced by the following procedure 8 ml of hydrazine hydrate is added to a suspension of 32.1 g of 5-o-chlorophenyl-7-ethyl-1,2-dihydro-3H-thieno[2,3-e] [1,4]diazepine-2-thione in 200 ml of methanol. Several minutes of stirring turns the suspension into a homogenous, red, transparent solution. Then, crystals begin to precipitate. After stirring at room temperature for 2 hours and subsequent ice-cooling, the cyrstals are collected by suction filtration and washed well with methanol to give 28.6 g of almost pure title compound appearing as yellow crystals. The product, when recrystallized from a mixture of ethanol and dimethylformamide, shows a melting point of 214°–216° C (decomposition).

c. 3 g of 2-(4-methylsemicarbazido)-5-o-chlorophenyl-7-ethyl-3H-thieno[2,3-e][1,4]diazepine is heated with stirring at 220° C for 20 minutes. After the evolution of gas ceases, the reaction mixture is cooled and treated with ligroin to give red-brown crystals. The crude crystals are recrystallized from a mixture of toluene and ligroin by use of decolorizing charcoal. Thus, there is obtained the title compound appearing as white crystals, melting at 199°–200° C.

The starting compound, 2-(4-methylsemicarbazido)-5-o-chlorophenyl-7-ethyl-3H-thieno[2,3-e][1,4]diazepine can be produced by the following procedure 1.1 ml of methyl isocyanate is added to a suspension of 5 g of 2-hydrazino-5-o-chlorophenyl-7-ethyl-3H-thieno[2,3-e][1,4]diazepine in 100 ml of tetrahydrofuran, and the resulting mixture is stirred at room temperature for 2 hours. Then the reaction mixture is poured into ice water, and the precipitated crystals are collected by filtration, washed with water, dried, and recrystallized from a mixture of chloroform and ligroin to give 2-(4-methylsemicarbazido)-5-o-chlorophenyl-7-ethyl-3H-thieno[2,3-e][1,4]diazepine, melting at 213°–215° C.

EXAMPLE 2

2-Methyl-6-o-chlorophenyl-8-ethyl-1,2-dihydro-4H-s-triazolo[3,4-c]-thieno[2,3-e][1,4]diazepin-1-one 4 g of 2-(2-ethoxycarbonyl-2-methylhydrazino)-5-o-chlorophenyl-7-ethyl-3H-thieno[2,3-e][1,4]diazepine is dissolved in 40 ml pyridine, and 0.4 g of sodium methoxide is added, and the resulting mixture is refluxed for 4 hours. Then the pyridine is removed under reduced pressure, and the residue is extracted with chloroform. The extract is washed successively with water, diluted hydrochloric acid, water and then an aqueous sodium hydrogen carbonate solution, and dried over anhydrous magnesium sulfate, and the chloroform is removed under reduced pressure. The residue is purified by silica gel column chromatography using 70–325 mesh silica gel and chloroform as an eluent. The fractions containing the objective compound are concentrated under reduced pressure to give a yellow jelly-like substance. The substance is dissolved in ethyl acetate, and to the solution there is added an ethanolic hydrochloric acid solution. The precipitated yellow crystals are recrystallized from a mixture of acetone and ethanol to give the title compound as hydrochloride containing 1/2 molecule of acetone for crystallization, melting at 186°–188° C.

The starting compound, 2-(2-ethoxycarbonyl-2-methylhydrazino)-5-o-chlorophenyl-7-ethyl-3H-thieno[2,3-e][1,4]diazepine can be produced by the following procedure 5 g of 2-(2-methylhydrazino)-5-o-chlorophenyl-7-ethyl-3H-thieno-[2,3-e][1,4]diazepine is dissolved in 30 ml of chloroform and a solution of 1.8 g of ethyl chlorocarbonate in 10 ml of chloroform is added dropwise with stirring, and the resulting mixture is stirred at room temperature for 2 hours. Then the reaction mixture is washed successively with water, an aqueous sodium hydrogen carbonate solution and water, and dried over anhydrous magnesium sulfate, and the chloroform is removed under reduced pressure. The residue is dissolved in ligroin, and the solution is allowed to stand overnight in a refrigerator to give 2-(2-ethoxycarbonyl-2-methylhydrazino)-5-o-chlorophenyl-7-ethyl-3H-thieno[2,3-e][1,4]diazepine appearing as pale yellow crystals, melting at 172°–174° C.

EXAMPLE 3

2,8-Dimethyl-6-o-chlorophenyl-1,2-dihydro-4H-s-triazolo [3,4-c]-thieno[2,3-e][1,4]diazepin-1-one 1 g of 6-o-chlorophenyl-8-methyl-1,2-dihydro-4H-s-triazolo[3,4-c]-thieno[2,3-e][1,4]diazepin-1-one is dissolved in 25 ml of dimethylformamide, and 0.09 g of sodium hydride (50% in mineral oil) is added, and the resulting mixture is heated at 60° C on a water bath with stirring for 30 minutes. After cooling to room temperature, a solution of 0.6 g of methyl iodide in 5 ml of ether is added dropwise, and the whole mixture is stirred at room temperature for 7 hours. Then the reaction mixture is poured into ice water, the precipitated crystals are filtered off, and the filtrate is extracted with chloroform. The extract is washed with water, dried over anhydrous magnesium sulfate, and the chloroform is removed under reduced pressure. The residue is recrystallized from a mixture of ligroin and ethanol to give the title compound as white crystals, melting at 199°–200° C.

EXAMPLE 4

2-Methylcarbamoyl-6-o-chlorophenyl-8-ethyl-1,2-dihydro-4H-s-triazolo[3,4-c]thieno[2,3-e][1,4]diazepin-1-one 9 g of 6-o-chlorophenyl-8-ethyl-1,2-dihydro-4H-s-triazolo [3,4-c]-thieno[2,3-e][1,4]diazepin-1-one is dissolved in 50 ml of chloroform, and 5 ml of methyl isocyanate is added, and the resulting mixture is refluxed for 8 hours. Then the chloroform is removed under reduced pressure, and the remaining jelly-like substance is treated with ligroin to give the title compound as white crystals. The product, when recrystallized from a mixture of ethanol and chloroform, shows a melting point of 193°–194° C.

EXAMPLE 5

2-(2-Dimethylaminoethyl)-6-o-chlorophenyl-8-ethyl-1,2-dihydro-4H-s-triazolo[3,4-c]thieno[2,3-e][1,4]diazepin-1-one 10 g of 6-o-chlorophenyl-8-ethyl-1,2-dihydro-4H-s-triazolo[3,4-c]thieno[2,3-e][1,4]diazepin-1-one is dissolved in 70 ml of dimethylformamide, and 1.9 g of sodium methoxide is added, and the resulting mixture is stirred at 60° C for 30 minutes. After cooling, a solution of 3.1 g of 2-dimethylaminoethyl chloride in 10 ml of dimethylformamide is added dropwise, and the whole mixture is stirred at 60° C for 3 hours. After cooling, the reaction mixture is poured into ice water, and the resulting aqueous mixture is extracted with toluene. The toluene extract is washed well with water, and dried over anhydrous magnesium sulfate, and the toluene is removed under reduced pressure. The remaining jelly-like substance is dissolved is ethyl acetate, and the solution is treated with ethanilic hydrochloric acid to give the dihydrochloride of the title compound appearing as pale yellow crystals. The product when recrystallized from a mixture of ethanol and ethyl acetate, shows a melting point of 221°–223° C.

Using the procedure set forth in the above examples, but substituting equivalent amounts of the appropriate starting materials, the following compounds are also produced 1. 6-o-chlorophenyl-8-ethyl-1,2-dihydro-4H-s-triazolo[3,4-c]thieno-[2,3-e][1,4]diazepine-1-thione, melting at 236°–237° C.
2. 6-o-chlorophenyl-8-methyl-1,2-dihydro-4H-s-triazolo [3,4-c]-thieno[2,3-e][1,4]diazepin-1-one, melting at 213°–215° C.
3. 6-phenyl-8-ethyl-1,2-dihydro-4H-s-triazolo[3,4-c]thieno[2,3-e]-[1,4]diazepin-1-one hydrochloride, melting at 276°–278° C.
4. 6-o-tolyl-8-ethyl-1,2-dihydro-4H-s-triazolo[3,4-c]thieno [2,3-e]-[1,4]diazepin-1-one, melting at 158°–160° C.
5. 6-o-methoxyphenyl-8-ethyl-1,2-dihydro-4H-s-triazolo[3,4-c]-thieno[2,3-e][1,4]diazepin-1-one, melting at 193°–194° C.
6. 6-o-bromophenyl-8-ethyl-1,2-dihydro-4H-s-triazolo [3,4-c]thieno-[2,3-e][1,4]diazepin-1-one, melting at 219°–220° C.
7. 6-o-chlorophenyl-7,8-dimethyl-1,2-dihydro-4H-s-triazolo[3,4-c]-thieno[2,3-e][1,4]diazepin-1-one, melting at 212°–214° C.
8. 6-o-chlorophenyl-1,2,7,8,9,10-hexahydro-4H-s-triazolo [3,4-c]-[1]benzothieno[2,3-e][1,4]diazepin-1-one, melting at 252°–254° C.
9. 6-o-fluorophenyl-8-ethyl-1,2-dihydro-4H-s-triazolo[3,4-c] thieno-[2,3-e][1,4]diazepin-1-one.
10. 6-m-trifluoromethylphenyl-8-ethyl-1,2-dihydro-4H-s-triazolo-[3,4-c]thieno[2,3-e][1,4]diazepin-1-one.
11. 2-methylcarbamoyl-6-o-chlorophenyl-7,8-dimethyl-1,2-dihydro-4H-s-triazolo[3,4-c]thieno[2,3-e][1,4]diazepin-1-one, melting at 169°–171° C.
12. 2-(2-dimethylaminoethyl)-6-o-chlorophenyl-7,8-dimethyl-1,2-dihydro-4H-s-triazolo[3,4-c]thieno[2,3-e][1,4]diazepin-1-one hydrochloride, melting at 262°–263° C.
13. 2-(3-dimethylaminopropyl)-6-o-chlorophenyl-8-ethyl-1,2-dihydro-4H-s-triazolo[3,4-c]thieno[2,3-e][1,4]diazepin-1-one oxalate 1/2 hydrate, melting at 125°–126° C.
14. 2-(3-pyrrolidinopropyl)-6-o-chlorophenyl-8-ethyl-1,2-dihydro-4H-s-triazolo[3,4-c]thieno[2,3-e][1,4]diazepin-1-one, melting at 104°–106° C.
15. 2-(3-piperidinopropyl)-6-o-chlorophenyl-8-ethyl-1,2-dihydro-4H-s-triazolo[3,4-c]thieno[2,3-e][1,4]diazepin-1-one, melting at 124°–125° C.
16. 2-(3-morpholinopropyl)-6-o-chlorophenyl-8-ethyl-1,2-dihydro-4H-s-triazolo[3,4-c]thieno[2,3-e][1,4]diazepin-1-one, melting at 137°–138° C.
17. 2-[3-(4-methyl-1-piperazinyl)propyl]-6-o-chlorophenyl-8-ethyl-1,2-dihydro-4H-s-triazolo[3,4-c]thieno[2,3-e][1,4]diazepin-1-one dimaleate, melting at 199°–200° C.
18. 2-(2-dimethylaminoethyl)-6-o-chlorophenyl-1,2,7,8,9,10-hexahydro-4H-s-triazolo[3,4-c][1]benzothieno[2,3-e][1,4]diazepin-1-one oxalate, melting at 146°–148° C.
19. 2-methylcarbamoyl-6-o-chlorophenyl-1,2,7,8,9,10-hexahydro-4H-s-triazolo[3,4-c][1]benzothieno[2,3-e][1,4]diazepin-1-one, melting at 223°–225° C.

Although the present invention has been adequately discussed in the foregoing specification and examples included therein, one of ordinary skill in the art readily recognizes that various changes and modifications may be made without departing from the spirit and scope thereof.

What is claimed is:
1. 6-o-Chlorophenyl-8-ethyl-1,2-dihydro-4H-s-triazolo[3,4-c]thieno[2,3-e] [1,4] diazepin-1-one.
2. 2-Methyl-6-o-chlorophenyl-8-ethyl-1,2-dihydro-4H-s-triazolo[3,4-c]thieno[2,3-e][1,4]diazepin-1-one.
3. 2,8-Dimethyl-6-o-chlorophenyl-1,2-dihydro-4H-s-triazolo[3,4-c]thieno [2,3-e]-[1,4]diazepin-1-one.
4. 6-o-Chlorophenyl-8-methyl-1,2-dihydro-4H-s-triazolo[3,4-c]thieno[2,3-e] [1,4]-diazepin-1-one.
5. 6-o-Bromophenyl-8-ethyl-1,2-dihydro-4H-s-triazolo[3,4-c]thieno[2,3-e] [1,4]-diazepin-1-one.
6. 6-o-Chlorophenyl-7,8-dimethyl-1,2-dihydro-4H-s-triazolo[3,4-c]thieno[2,3-e][1,4]diazepin-1-one.

* * * * *